(12) United States Patent
Zhou et al.

(10) Patent No.: US 11,441,700 B2
(45) Date of Patent: Sep. 13, 2022

(54) VALVE COOLING AND NOISE SUPPRESSION

(71) Applicant: Alcon Inc., Fribourg (CH)

(72) Inventors: Jiansheng Zhou, Cerritos, CA (US); Craig Fritch, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 134 days.

(21) Appl. No.: 16/844,145

(22) Filed: Apr. 9, 2020

(65) Prior Publication Data

US 2020/0340600 A1    Oct. 29, 2020

Related U.S. Application Data

(60) Provisional application No. 62/837,801, filed on Apr. 24, 2019.

(51) Int. Cl.

| F16K 49/00 | (2006.01) |
|---|---|
| F16K 27/12 | (2006.01) |
| F16K 47/02 | (2006.01) |
| A61F 9/007 | (2006.01) |
| G05D 16/20 | (2006.01) |
| A61B 17/00 | (2006.01) |

(52) U.S. Cl.
CPC .......... *F16K 49/00* (2013.01); *A61F 9/00736* (2013.01); *F16K 27/12* (2013.01); *F16K 47/02* (2013.01); *A61B 2017/00544* (2013.01); *G05D 16/2024* (2019.01)

(58) Field of Classification Search
CPC . Y10T 137/6525; F16K 49/00; F16K 49/005; F16K 27/12; F16K 47/02; A61F 9/00736; A61B 2017/00544; G05D 16/2024

USPC ......................................................... 137/884
See application file for complete search history.

(56) References Cited

U.S. PATENT DOCUMENTS

| 2,077,995 A | 4/1937 | Wilson | |
| 2,157,480 A * | 5/1939 | Cole | ..................... F02M 53/04 251/129.21 |
| 4,453,565 A | 6/1984 | Neff | |

(Continued)

FOREIGN PATENT DOCUMENTS

| EP | 0358134 A1 * | 3/1990 | ............. F16K 49/00 |
| WO | WO9902089 A1 | 1/1999 | |
| WO | WO-2008142263 A2 * | 11/2008 | ............. F02M 26/51 |

OTHER PUBLICATIONS

Machine Translation of WO2008142263 retrieved from espacenet.com Oct. 2021. (Year: 2021).*

(Continued)

*Primary Examiner* — Jessica Cahill

(57) ABSTRACT

Certain embodiments provide a cover mounted on top of a manifold, the cover comprising an exhaust opening and an inner surface forming a space between the inner surface of the cover and an outer surface of the manifold, wherein the space is configured to receive pressurized gas at an inlet positioned on a first side of a valve. The valve is coupled to the outer surface of the manifold and positioned within the space. The exhaust opening is positioned on a second side of the valve opposite the first side of the valve such that pressurized gas circulates from the inlet around the valve and exits through the exhaust opening.

18 Claims, 13 Drawing Sheets

(56) References Cited

U.S. PATENT DOCUMENTS

| | | | | |
|---|---|---|---|---|
| 4,478,241 | A | * | 10/1984 | Cardenas-Franco .... C03B 9/406 |
| | | | | 137/338 |
| 4,538,643 | A | * | 9/1985 | Goedecke ........... F15B 13/0438 |
| | | | | 137/625.64 |
| 6,117,150 | A | * | 9/2000 | Pingleton ......... A61B 17/00234 |
| | | | | 606/167 |
| 6,158,454 | A | * | 12/2000 | Duret ...................... B08B 15/00 |
| | | | | 137/884 |
| 6,383,203 | B1 | * | 5/2002 | Makihara ........... A61F 9/00763 |
| | | | | 606/171 |
| 7,543,450 | B2 | | 6/2009 | Miura |
| 8,162,000 | B2 | | 4/2012 | Turner |
| 8,196,893 | B2 | | 6/2012 | Grout |
| 8,312,800 | B2 | | 11/2012 | Turner |
| 8,590,937 | B2 | | 11/2013 | Hino |
| 8,844,566 | B2 | | 9/2014 | Underwood |
| 9,180,232 | B2 | | 11/2015 | Williams |
| 9,241,830 | B2 | | 1/2016 | Olivera |
| 10,122,198 | B2 | | 11/2018 | Zhang |
| 10,139,004 | B2 | * | 11/2018 | Hironaka ................ F16K 49/00 |
| 10,383,766 | B2 | * | 8/2019 | Farley ................. A61M 39/227 |
| 10,962,143 | B2 | * | 3/2021 | Cis ...................... F16K 31/0682 |
| 2007/0270746 | A1 | * | 11/2007 | King .................... F16K 31/122 |
| | | | | 604/131 |
| 2011/0144675 | A1 | | 6/2011 | Gao |
| 2012/0310146 | A1 | * | 12/2012 | Easley ................ A61F 9/00736 |
| | | | | 604/22 |
| 2014/0171991 | A1 | * | 6/2014 | Lee ..................... A61F 9/00763 |
| | | | | 606/167 |
| 2016/0296370 | A1 | | 10/2016 | Farley |
| 2017/0304116 | A1 | | 10/2017 | Gerg |
| 2019/0331256 | A1 | * | 10/2019 | Zak ........................ H02K 26/00 |
| 2021/0247154 | A1 | * | 8/2021 | Walker ................. F28F 21/081 |

OTHER PUBLICATIONS

Machine Translation of EP0358134A1 retrieved from espacenet.com Oct. 2021. (Year: 2021).*

* cited by examiner

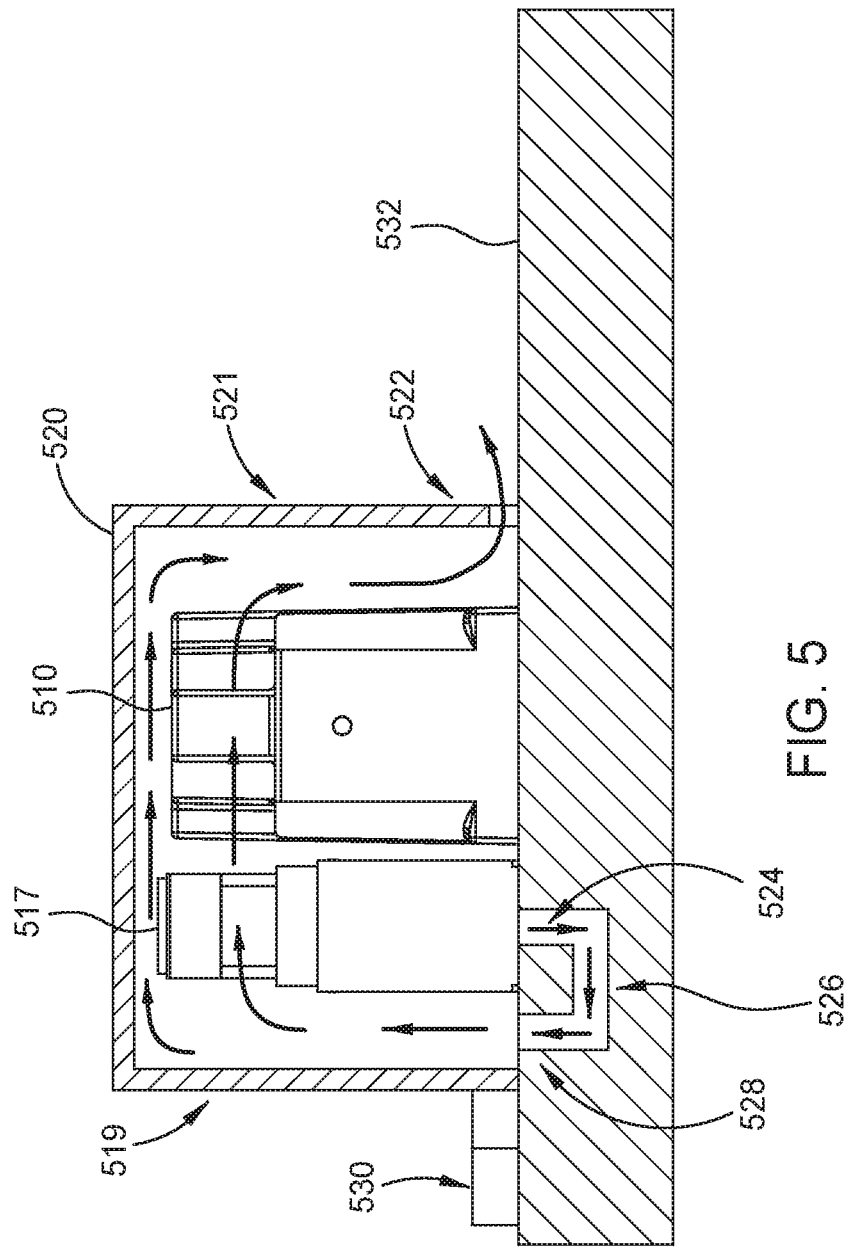

VALVE COOLING AND NOISE SUPPRESSION

PRIORITY CLAIM

This application claims the benefit of priority of U.S. Provisional Patent Application Ser. No. 62/837,801 titled "VALVE COOLING AND NOISE SUPPRESSION," filed on Apr. 24, 2019, whose inventors are Jiansheng Zhou and Craig Fritch, which is hereby incorporated by reference in its entirety as though fully and completely set forth herein.

TECHNICAL FIELD

The present disclosure relates generally to valve cooling and noise suppression.

BACKGROUND

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV (Cytomegalovirus) retinitis, and many other ophthalmic conditions.

The vitreous is a normally clear, gel-like substance that fills the center of the eye. It may make up approximately two-thirds of the eye's volume, giving it form and shape before birth. Certain problems affecting the back of the eye may require a vitrectomy, or surgical removal of the vitreous. Removal of vitreous can involve a vitrector (also referred to as the "cutter" or "vitreous cutter"), that works like a tiny guillotine, with an oscillating microscopic cutter to remove the vitreous gel in a controlled fashion. The cutter is powered by a pneumatic vitrectomy machine including one or more pneumatic valves (also referred to as drive valves). In certain cases, one or more of the pneumatic valves may be operated at both a very high input voltage and at high speed. Operating a pneumatic valve at such high input voltage and speed, however, causes the pneumatic valve to heat up excessively and generate very loud noises.

BRIEF SUMMARY

The present disclosure relates generally to valve cooling and noise suppression.

Certain embodiments provide a cover mounted on top of a manifold, the cover comprising an exhaust opening and an inner surface forming a space between the inner surface of the cover and an outer surface of the manifold, wherein the space is configured to receive pressurized gas at an inlet positioned on a first side of a valve. The valve is coupled to the outer surface of the manifold and positioned within the space. The exhaust opening is positioned on a second side of the valve opposite the first side of the valve such that pressurized gas circulates from the inlet around the valve and exits through the exhaust opening.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

FIG. 5 illustrates a cross-sectional view of an example cover that is mounted on top of a manifold in which a pneumatic system is incorporated, in accordance with certain embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Figure 1:
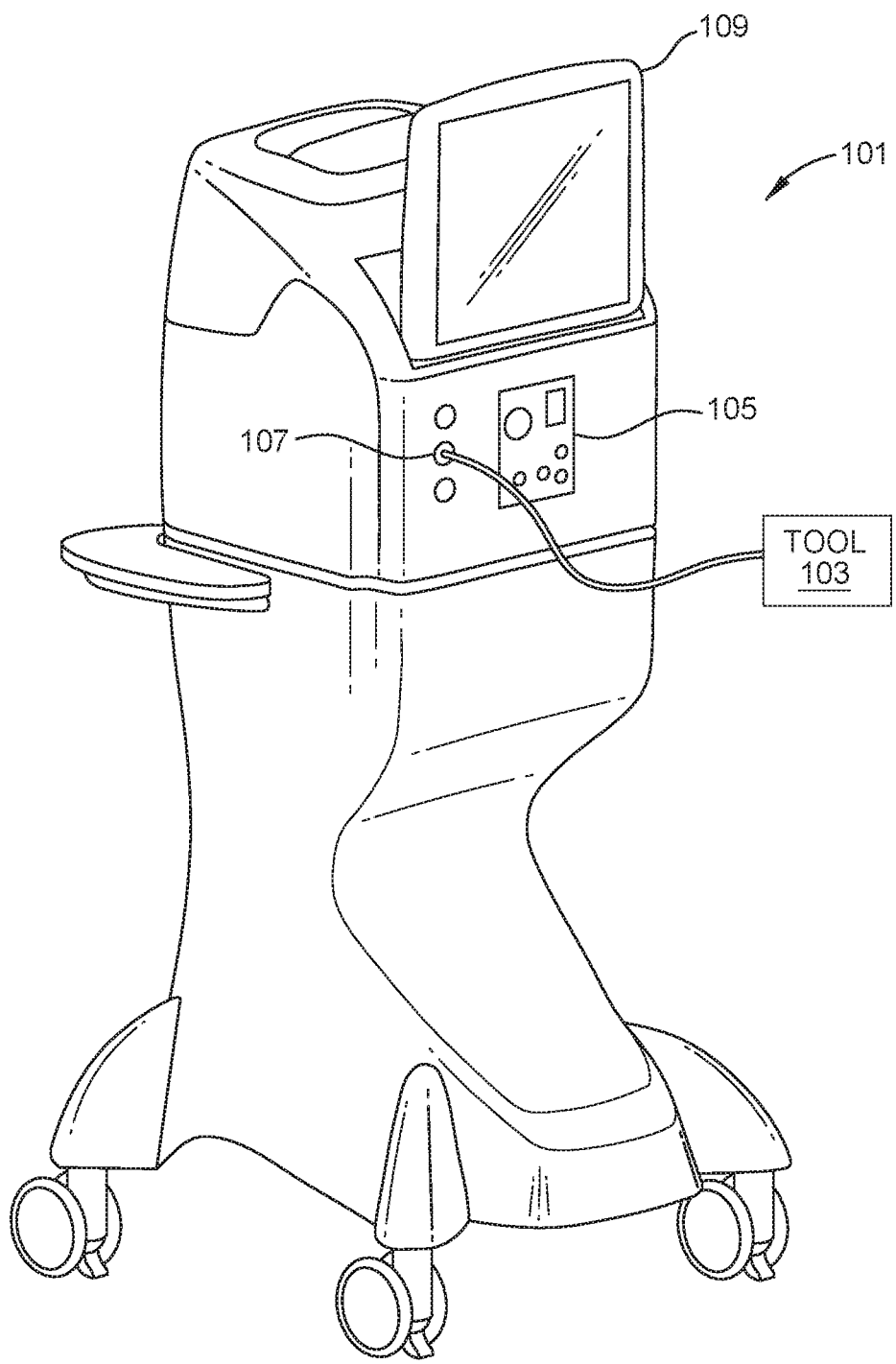
FIG. 1 illustrates an embodiment of a surgical console for a pneumatically powered ophthalmic surgical machine, in accordance with certain embodiments.

FIG. 1 illustrates an embodiment of a surgical console 101 for a pneumatically powered ophthalmic surgical machine. The surgical console 101 may be configured to drive one or more pneumatic tools 103. The tools 103 may include, for example, scissors, vitrectors, forceps, and injection or extraction modules. Other tools 103 may also be used. In operation, the pneumatically powered ophthalmic surgery machine of FIG. 1 may operate to assist a surgeon in performing various ophthalmic surgical procedures, such as a vitrectomy. A compressed gas, such as nitrogen, may provide the power through the surgical console 101 to power tools 103. The surgical console 101 may include a display 109 for displaying information to a user (the display may also incorporate a touchscreen for receiving user input). The surgical console 101 may also include a fluidics module 105 (e.g., to support irrigation/aspiration functions) and one or more port connectors 107 for coupling to tools 103 (e.g., coupling through pneumatic lines attached to the tools 103).

Figure 2A:
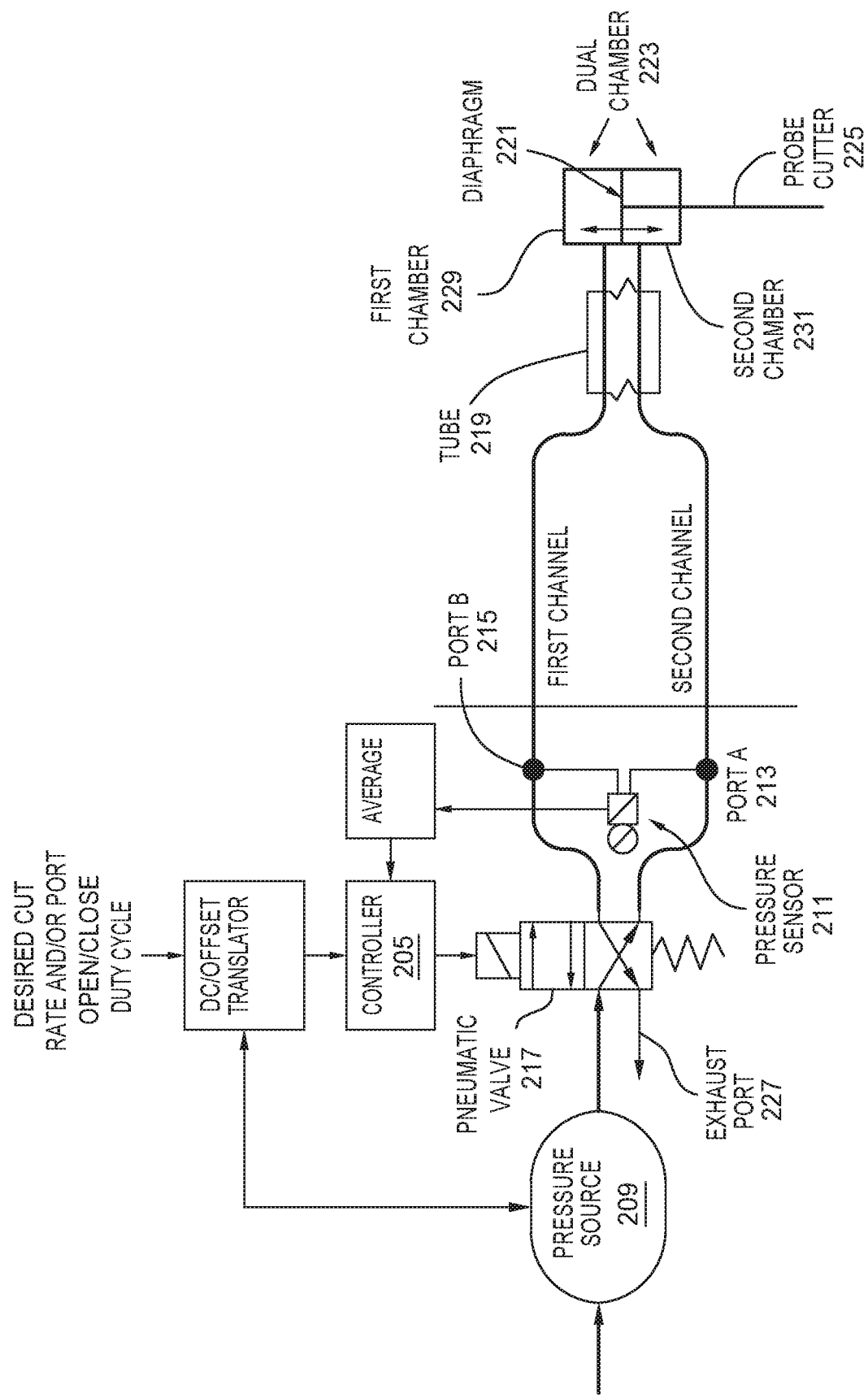
FIGS. 2A and 2B illustrate a schematic of a pneumatic system for a pneumatically powered vitrectomy machine, in accordance with certain embodiments.
Figure 2B:
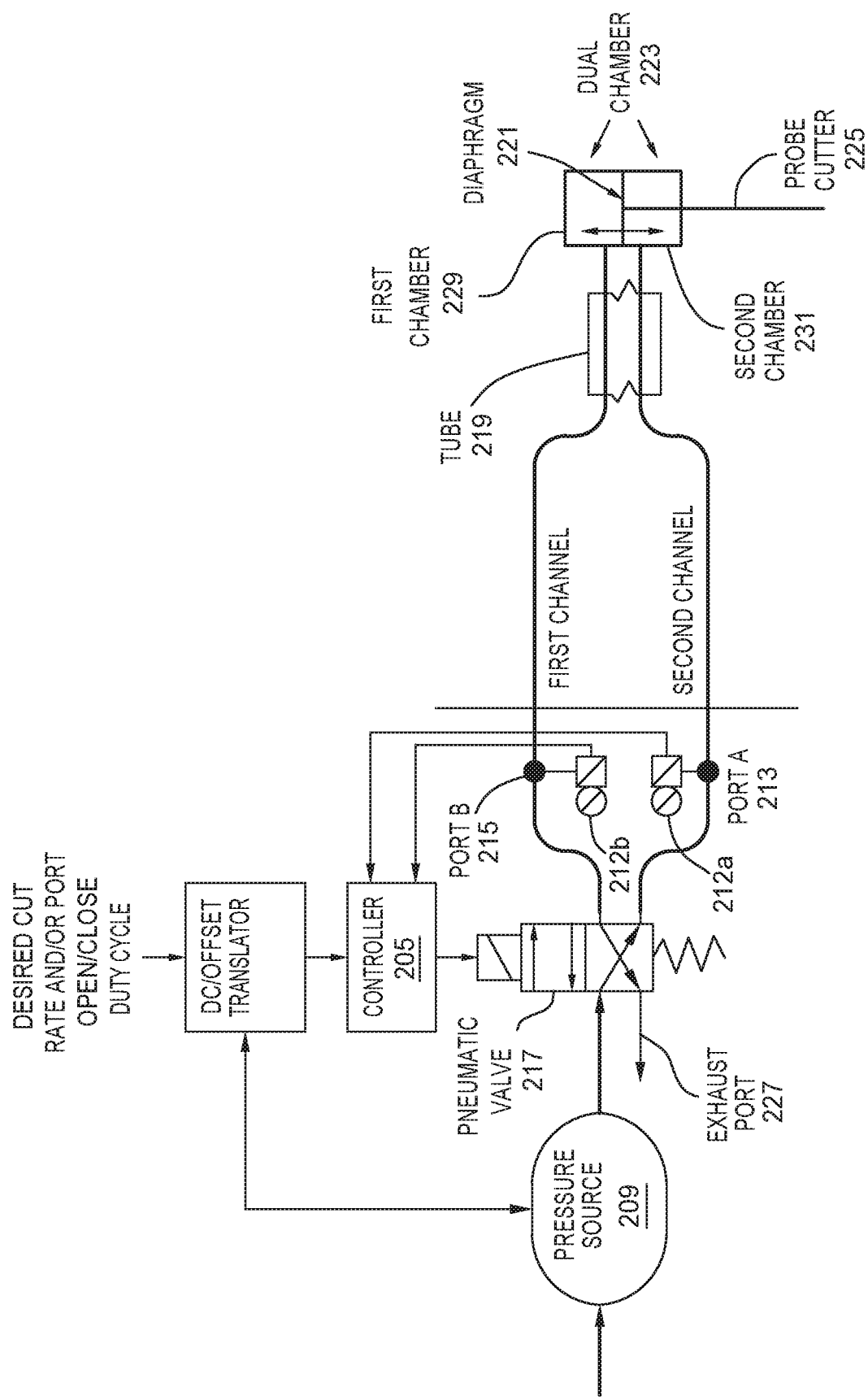

FIGS. 2A and 2B illustrate a schematic of a pneumatic system for a pneumatically powered vitrectomy machine. As seen in FIGS. 2A and 2B, the pneumatic system may include a pneumatic valve 217 coupling a pressure source 209 (e.g., a regulated pressure source such as a gas cylinder or a wall outlet gas supply) to output port A 213 and output port B 215 (the output port A 213 and output port B 215 may be coupled to the tool 103 through one or more port connectors 107). In some embodiments, the pneumatic valve 217 may be controlled by controller 205. In some embodiments, the pressure of the pressure source 209 may also be regulated by controller 205 or a separate controller (e.g., internal to the surgical console 101). The controller 205 may regulate pressure (e.g., to balance between lower pressures for reducing gas consumption and higher pressures for faster cut rates and/or to increase a dynamic range of available cut rates). In some embodiments, the components of the pneumatic system may be incorporated in one or more manifolds (e.g., machined out of a metal, such as aluminum) or manifold plates. The manifolds may be gas tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 101.

The valve 217 may include a solenoid that operates to move the valve 217 to one of the two positions (e.g., see FIGS. 2A-B) as directed by control signals from controller 205. In a first position, pneumatic valve 217 may allow pressurized gas to pass through pneumatic valve 217 to output port B 215 to provide pneumatic power to the probe cutter 225 while venting pressurized gas from output port A 213 through an exhaust port 227. In a second position, the pneumatic valve 217 may provide pressurized gas to output port A 213 and vent pressurized gas from output port B 215 through the exhaust port 227. In this position, pressurized gas may pass through output port A 213 to provide pneumatic power to a tool 103 (e.g., probe cutter 225). Thus, when the pneumatic valve 217 is in the first position, the first chamber 229 of the dual chambers 223 may be charged while the second chamber 231 may be discharged. When the pneumatic valve 217 is in the second position, the second chamber 231 may be charged while the first chamber 229 may be discharged. Note that in the pneumatic system shown in FIG. 2A only a single pressure sensor 211 is used while in the pneumatic system shown in FIG. 2B two pressure sensors 212a and 212b are used. Also, although an isolation valve is not shown in FIGS. 2A and 2B, in certain aspects, an isolation valve may be coupled to pneumatic valve 217 to provide pressurized gas to pneumatic valve 217 or stop the flow of pressurized gas to pneumatic valve 217.

Figure 3:
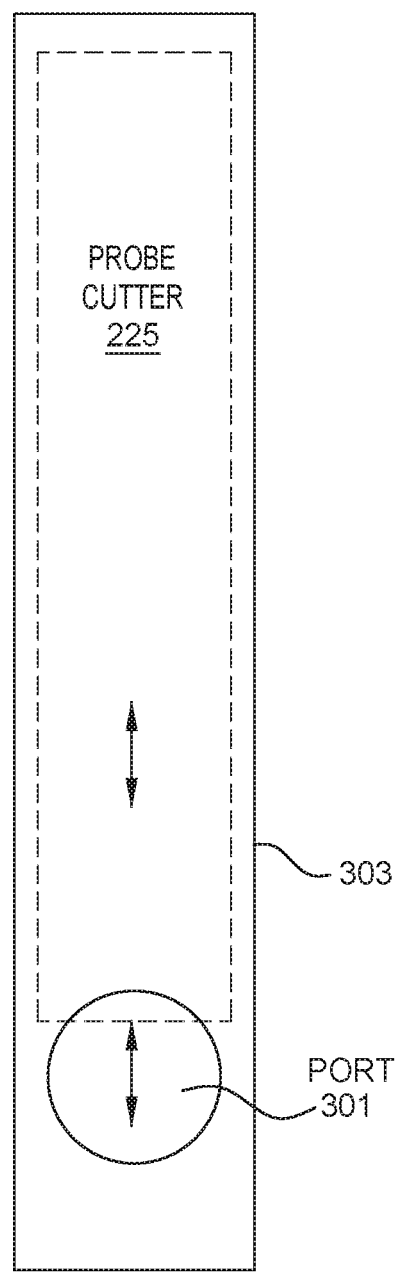
FIG. 3 illustrates the cutting device of a surgical probe.

As seen in FIG. 3, the probe cutter 225 may act as a cutting device. The probe cutter 225 may reciprocate inside an outer tube 303 with a cutter port 301 (e.g., the probe cutter 225 may be moved by a diaphragm 221 that in turn oscillates as pressurized gas is alternately directed to output ports A and B (and into respective chambers of the dual chamber 223)). In some embodiments, probe cutter 225 may be attached to output ports A and B through tube 219 (separate tubes for each port may also be used). As the probe cutter 225 moves back and forth, the probe cutter 225 may alternately open and close cutter port 301 with a sharpened tip of the probe cutter 225. Each cycle of the probe cutter 225 through outer tube 303 may cut through material such as vitreous in the cutter port 301 as the probe cutter 225 is closing. A port duty cycle (PDC) may indicate the amount of time the cutter port 301 is open and closed. For example, a PDC of 49% may indicate the cutter port 301 is open 49% of the cycle time (and closed 51% of the cycle time-the cycle time being, for example, the amount of time between each successive opening of the cutter port 301).

In some embodiments, the valve duty cycle (VDC) may include the amount of time the pneumatic valve 217 is in the first and second positions. In some embodiments, a cut rate of the probe cutter 225 may be controlled by the controller 205 through valve 217. For example, to provide a 2500 cuts per minute probe rate, controller 205 may direct pneumatic valve 217 to provide pressurized gas alternately to port A (second channel) and port B (first channel) at a rate of approximately 24 milliseconds (ms) per cycle. To obtain a cut rate of 2500 cuts per minute, the two pneumatic channels may cycle open/closed every 24 ms (2500 cuts/min or 1 min/2500 cuts*60 seconds/1 min=0.024 seconds/cut=24 ms/cut), which may open for 12 ms to each channel.

For the benefit of reducing traction (which can cause retinal detachment) during vitrectomy procedure, the vitrectomy probe is desired to be operated at high speed. The common understanding is the faster the better. Therefore pneumatic valve 217 is often operated at its maximum speed (in CPM). At very high speed, each valve cycle time is very short, which requires the solenoid valve to move very fast in opening and closing. For example, at 15,000 cpm with 50% VDC, in each valve cycle the time duration of valve open and close is only 2 ms. Therefore the solenoid valve has to actuate very fast so that it opens and closes in less than 2 ms.

In some cases, increasing solenoid power by coil design and/or applying higher voltage along with a stronger return spring can speed up the valve actuation. However, increasing speed can reduce the reliability of pneumatic valve 217. This is because as the number of valve cycles increases over a given time period, the valve operating condition may worsen at higher speeds due to higher mechanical impact as well as heat that is generated by the solenoid coil. In other words, the usage life of the pneumatic valve 217 can be reduced when it is operated at higher speed (in CPM).

To enhance reliability of vitrectomy instruments, in certain cases, a redundant pneumatic circuit may be used, which provides a backup pneumatic valve (BPV). As such, when the primary pneumatic valve, such as pneumatic valve 217, fails or malfunctions, the system automatically switches to the backup pneumatic circuit, which operates the BPV instead.

Figure 4A:
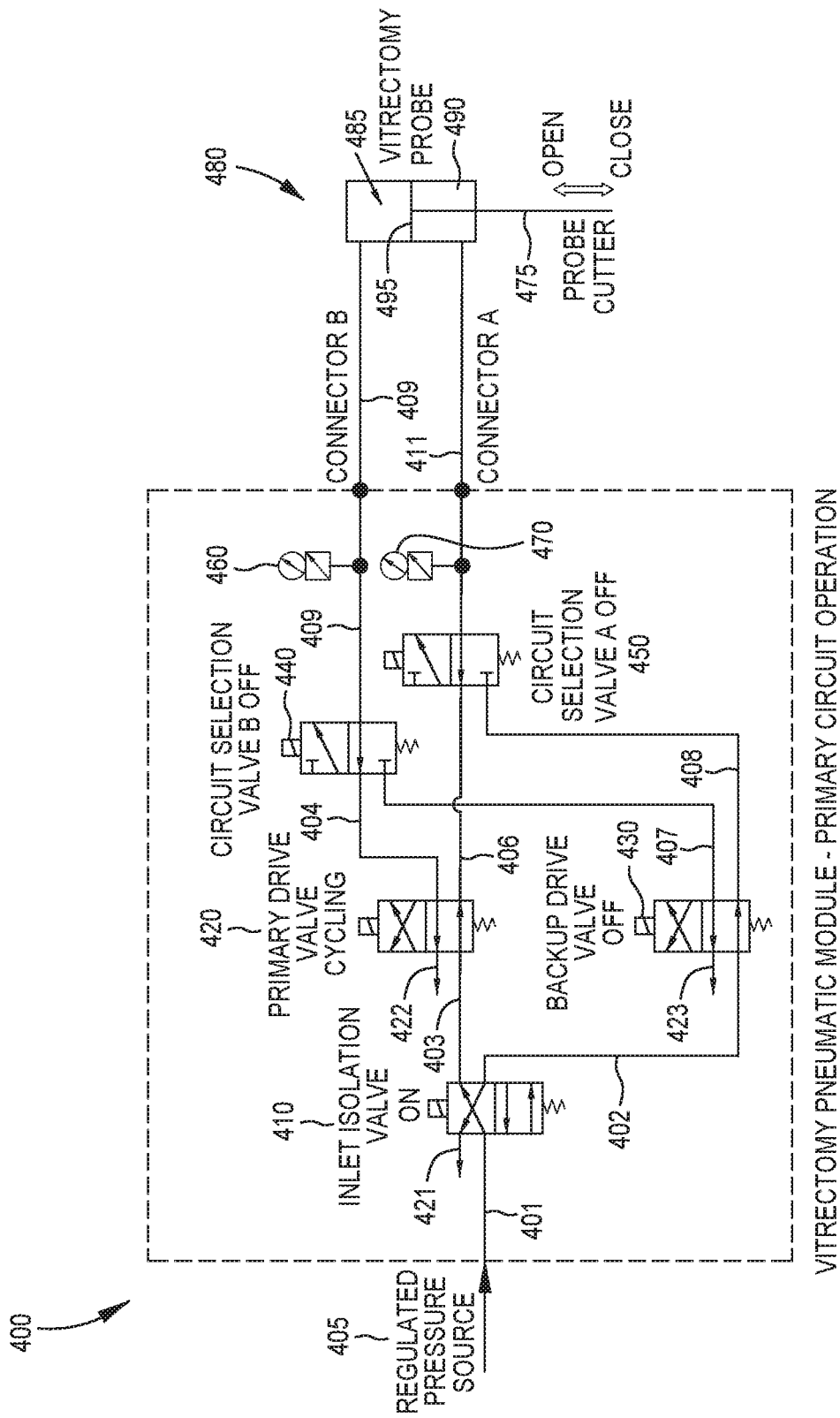
FIGS. 4A and 4B illustrate a redundant pneumatic circuit in a primary mode and a backup mode respectively, in accordance with certain embodiments.

FIG. 4A illustrates a redundant pneumatic circuitry 400 including a primary pneumatic valve (PPV) 420 in operation and a backup pneumatic valve (BPV) 430 that can be engaged to power a vitrectomy probe 480 when the PPV 420 fails. The redundant pneumatic circuitry 400 includes a source of regulated pneumatic pressure 405 (e.g. compressed gas canister, hospital wall gas, etc.) and tubing 401, 402, 403, 404, 406, 407, 408, 409, and 411 for fluidly coupling the components of the redundant pneumatic circuitry 400 with the vitrectomy probe 480.

The source of regulated pneumatic pressure 405 is fluidly coupled with an isolation valve 410 via tubing 401. As shown in FIG. 4A, the isolation valve 410 is a four-way valve. The isolation valve 410 is fluidly coupled (via tubing 402, 403) to a PPV 420 and a BPV 430. Also, each of the PPV 420 and the BPV 430 are fluidly coupled (via tubing 404, 406, 407, and 408) to both of a first circuit selection valve 440 and a second circuit selection valve 450.

The first circuit selection valve 440 and the second circuit selection valve 450 are respectively coupled (via tubing 409, 411) to a first chamber 485 and a second chamber 490 of the vitrectomy probe 480. The first chamber 485 and the second chamber 490 are separated by a diaphragm 495 which is alternatively displaced when one of the PPV 420 or the BPV 430 alternatively drive and vent the chambers 485, 490. The diaphragm 495, in turn, drives the probe cutter 475 in a manner described above. The redundant pneumatic circuitry 400 includes exhaust ports 421, 422, 423 which vent pressurized fluid to atmosphere.

In this detailed description, the terms "off" and "on" in the context of the valves state are used as a convenience; however, the description of the valve states as "on" and "off" should not be read to imply functionality, non-functionality, etc.

Prior to a vitrectomy procedure, the isolation valve 410, the first circuit selection valve 440, and the second circuit selection valve 450 are all in an "off" state. When these valves are in an "off" state, the flow of the pneumatic pressure is suppressed from being delivered to the vitrectomy probe 480 by virtue of the isolation valve 410 delivering the pneumatic pressure through the BPV 430 and to the first and second circuit selection valves 440, 450, which block the flow of fluid in their "off" state from BPV 430.

At the initiation of a vitrectomy procedure, the inlet isolation 410 valve is actuated and put into an "on" state, which supplies pneumatic flow and pressure to the PPV 420. The PPV 420 cycles on/off at a specific rate (i.e. cuts per minute or CPM) and with specific valve duty cycle (VDC) determined by the user and system control software. The first and second circuit selection valves 440, 450 remain in their "off" state, which allow pneumatic flow and pressure from the PPV 420 to go through the first and second circuit selection valves 440, 450 and to respective chambers 485, 490 of the vitrectomy probe 480 and causes the probe cutter 475 to cut at the specified CPM.

The redundant circuitry 400 also includes two pressure sensors 460, 470 and one or more system controllers. The pressure sensors 460, 470 monitor pressure of the two channels of tubing 409, 411 in real time and the system controller receives and processes the pressure data in real time. The system controller can determine when the pressure is normal or abnormal by a variety of methods. For example, in some cases, the system controller can determine whether or not the pressure is normal by examining a differential pressure between channels monitored by the two pressure sensors 460, 470.

The system controller can examine the monitored channel pressures, calculate a differential pressure as the pressure from second pressure sensor 470 minus the pressure from the first pressure sensor 460, and report the differential pressure as being abnormal when the differential pressure exceeds a particular predetermined threshold. One particular method involves comparing peak open pressure and peak close pressure in the form of differential pressure as a second channel minus a first channel to normal open threshold and normal close threshold respectively. The system controller can report the pressure as normal when both absolute values of peak open pressure and peak close pressure are beyond the absolute values of normal open threshold and normal close threshold respectively. In this state of operation, the system controller allows the PPV 420 to continue to operate.

Conversely, if the system controller determines that the pressure is abnormal, the system controller can perform one or more remediation step in an attempt to adjust the pneumatic pressure back to an acceptable level. For example, the system controller can adjust primary drive 420 valve's duty cycle (VDC) to shift the peaks of open pressure and close pressure up or down. After performing the remediation step, the system controller can examine the pneumatic pressure from the pressure sensors 460, 470 and determine if the remediation step was successful. For example, if the VDC adjustment successfully brings the absolute values of peak open pressure and peak close pressure beyond the absolute values of normal open threshold and normal close threshold respectively, the system controller determines that the remediation step was successful and causes the PPV 420 to maintain operation. Conversely, when the system controller determines that the remediation step was unsuccessful, the system controller can cause the redundant circuitry 400 to switch the vitrectomy to a backup mode by switching to the BPV 430.

Figure 4B:
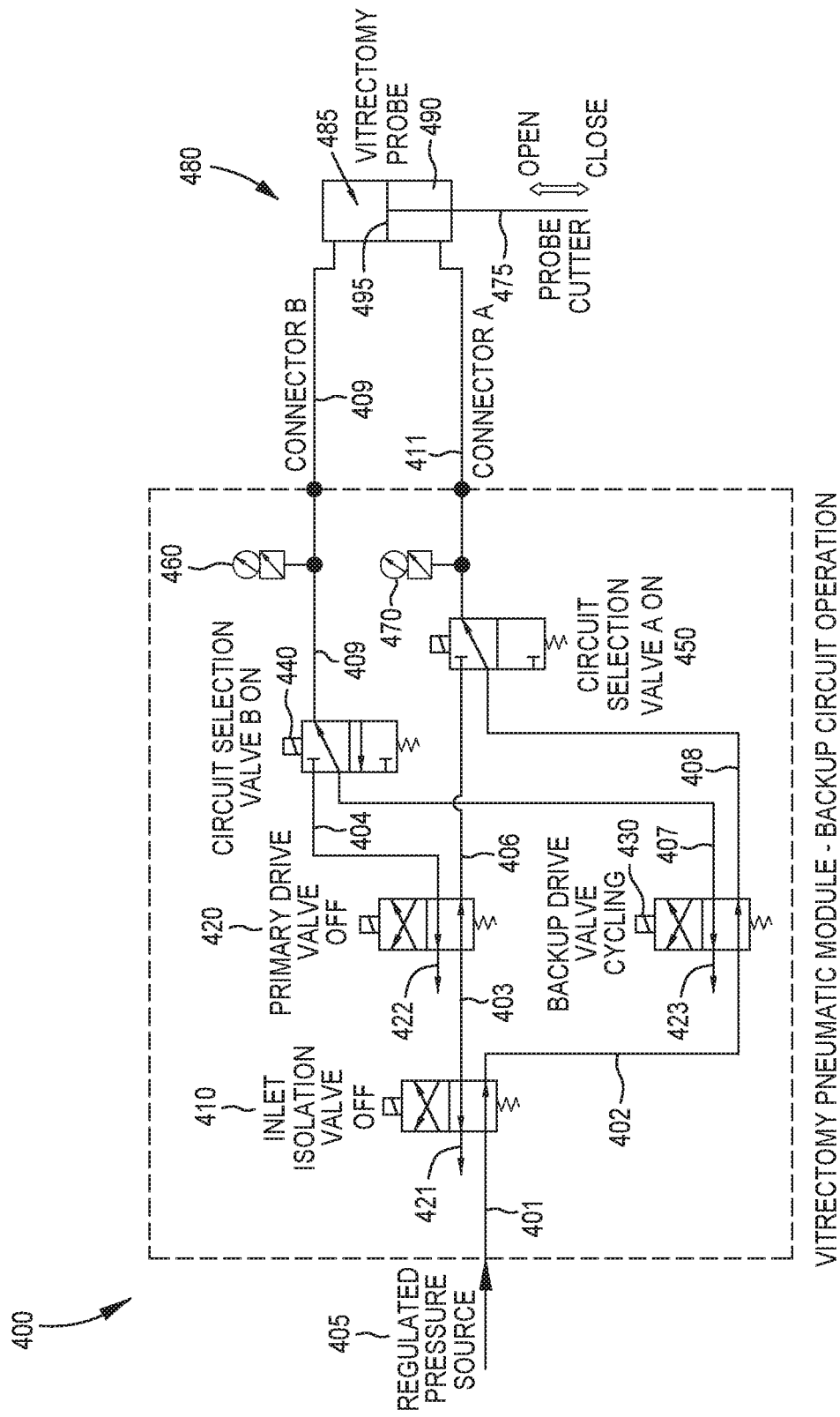

FIG. 4B illustrates the redundant pneumatic circuitry 400 with the BPV 430 engaged for powering the vitrectomy probe 480 after the system controller determines that PPV 420 failed. When the system controller switches the redundant pneumatic circuitry to the BPV 430, the inlet isolation valve is actuated and put into an "off" state, which supplies pneumatic flow and pressure to the BPV 430. The BPV 430 cycles on/off at a specific rate (i.e. cuts per minute or CPM) and with specific valve duty cycle (VDC) determined by the user and system control software. Also, the system controller actuates the first and second circuit selection valves 440, 450 to their "on" state, which allow pneumatic flow and pressure from the BPV 430 to go through the first and second circuit selection valves 440, 450 and to respective chambers 485, 490 of the vitrectomy probe 480 and causes the probe cutter 475 to cut at the specified CPM.

The pressure sensors 460, 470 can continue to monitor pressure of the two channels of tubing 409, 411 in real time and the system controller can continue to receive and process the pressure data in real time without interruption caused by the switch to backup mode. The system controller can determine when the pressure is normal or abnormal by a variety of methods. For example, in some cases, the system controller can determine whether the pressure is normal by examining a differential pressure between channels monitored by the two pressure sensors 460, 470.

The system controller can processes the pressure data of the two pressure sensors and determine when the pressure is normal or not, e.g. comparing peak open pressure and peak close pressure in the form of differential pressure as the second channel minus the first channel to normal open threshold and normal close threshold respectively. When the pressure is normal, the system controller can cause the BPV 430 to continue to operate. When the pressure is abnormal, the system controller can perform another remediation step, e.g. adjusting backup drive 430 valve's duty cycle (VDC) to shift the peaks of open and close pressure up or down. When the remediation step is successful in bringing the pressure back to normal, the system controller can cause the BPV 430 to maintain operation. When the remediation step is unsuccessful in bringing the pressure back to normal, the system controller can determine that an unresolvable system fault has occurred, and the system controller can shut down vitrectomy operation.

In addition, since the BPV 430 maintains the same vitrectomy operation as the PPV 420, the vitrectomy procedure is not interrupted or stopped and the service to resolve the PPV 420 failure or malfunction is not urgent.

Regardless of whether a BPV is used to provide redundancy, operating a pneumatic valve at a high valve cycle rate may cause the pneumatic valve to overheat and generate loud noise. For example, applying a high voltage to the solenoid coil within the pneumatic valve may cause the solenoid coil to excessively overheat and to actuate the corresponding solenoid plunger faster, which generates a much louder noise. Accordingly, certain embodiments described herein provide an exhaust cooling and muffler cover ("cover") for cooling a pneumatic valve's temperature using pressurized gas vented from the pneumatic valve's exhaust port while suppressing the noise associated with solenoid plunger and venting of the pressurized gas. In cases where a pneumatic system involves a redundant pneumatic circuitry with an insulation valve as well as a backup valve, certain embodiments described herein provide a cover for covering both the primary and the backup pneumatic valves and/or the isolation valve, as shown in FIGS. 5-10. In such embodiments, the pressurized gas cools both the pneumatic valve(s) and the isolation valve.

FIG. 5 illustrates a cross-sectional view of an example cover 520 that is mounted on top of manifold 532 in which a pneumatic system is incorporated. The pneumatic system described in relation to FIG. 5 involves a redundant pneumatic circuitry including an isolation valve 510, a PPV 517 and a BPV, which is not shown for simplicity. Also, the rest of the components of the redundant pneumatic circuitry, as described in relation to FIGS. 4A-4B, are not shown in FIG. 5 for brevity and simplicity. Cover 520 may comprise one or more plastic, metal, foam, rubber, or similar material.

Figure 8:
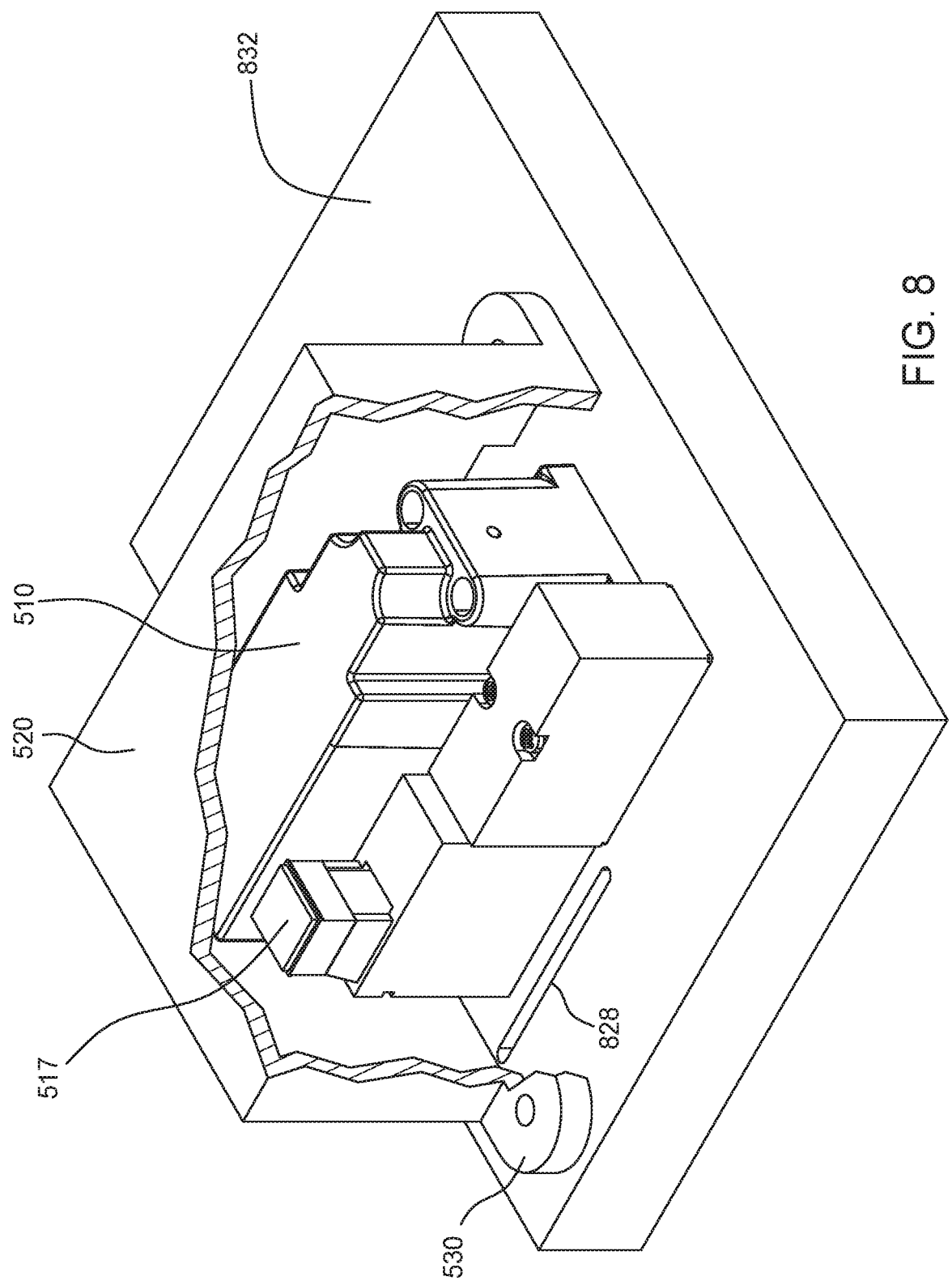
FIG. 8 illustrates an example inlet port that is slotted, in accordance with certain embodiments.
Figure 9:
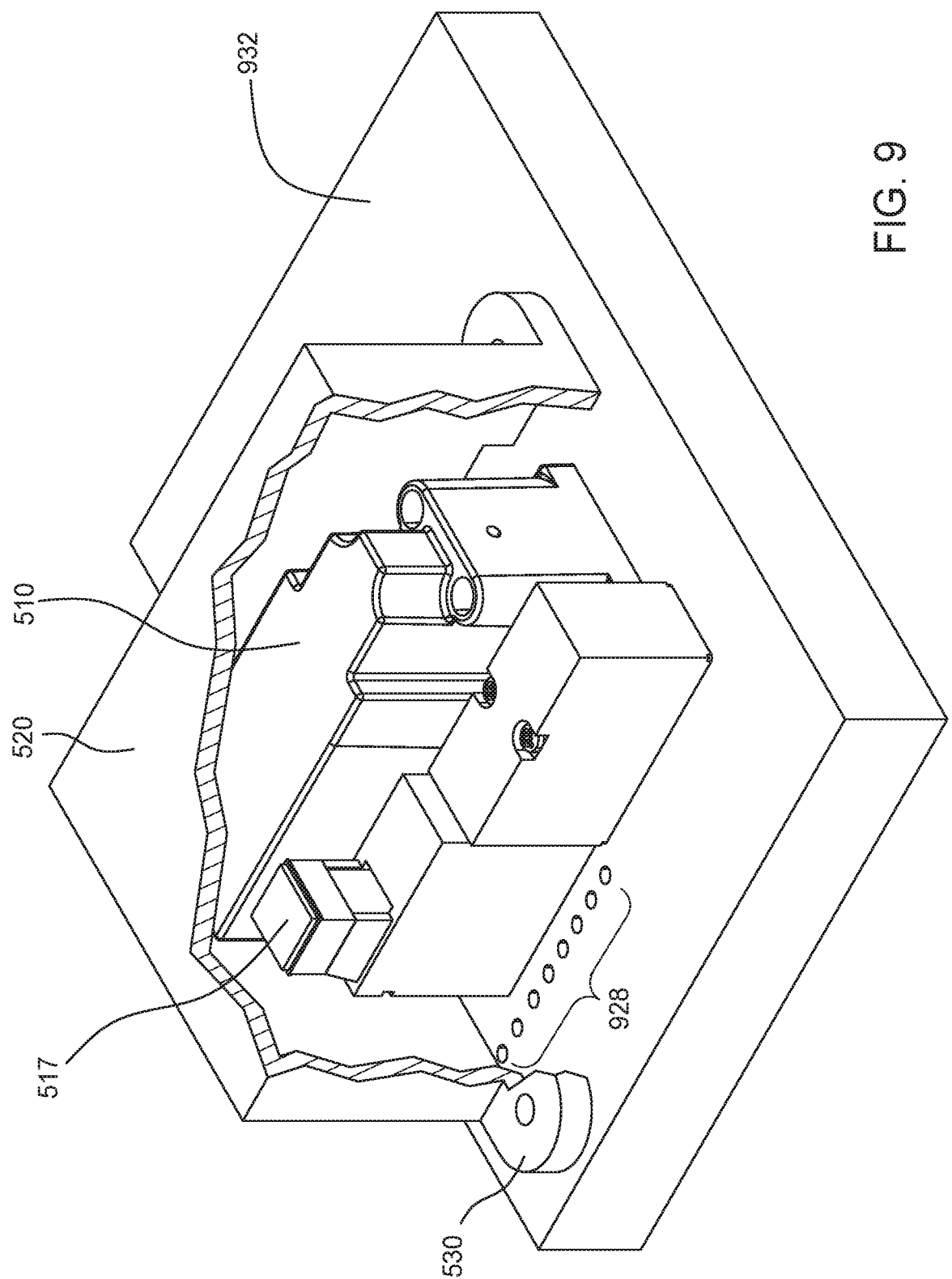
FIG. 9 illustrates example inlet ports that are arranged next to each other, in accordance with certain embodiments.
Figure 10:
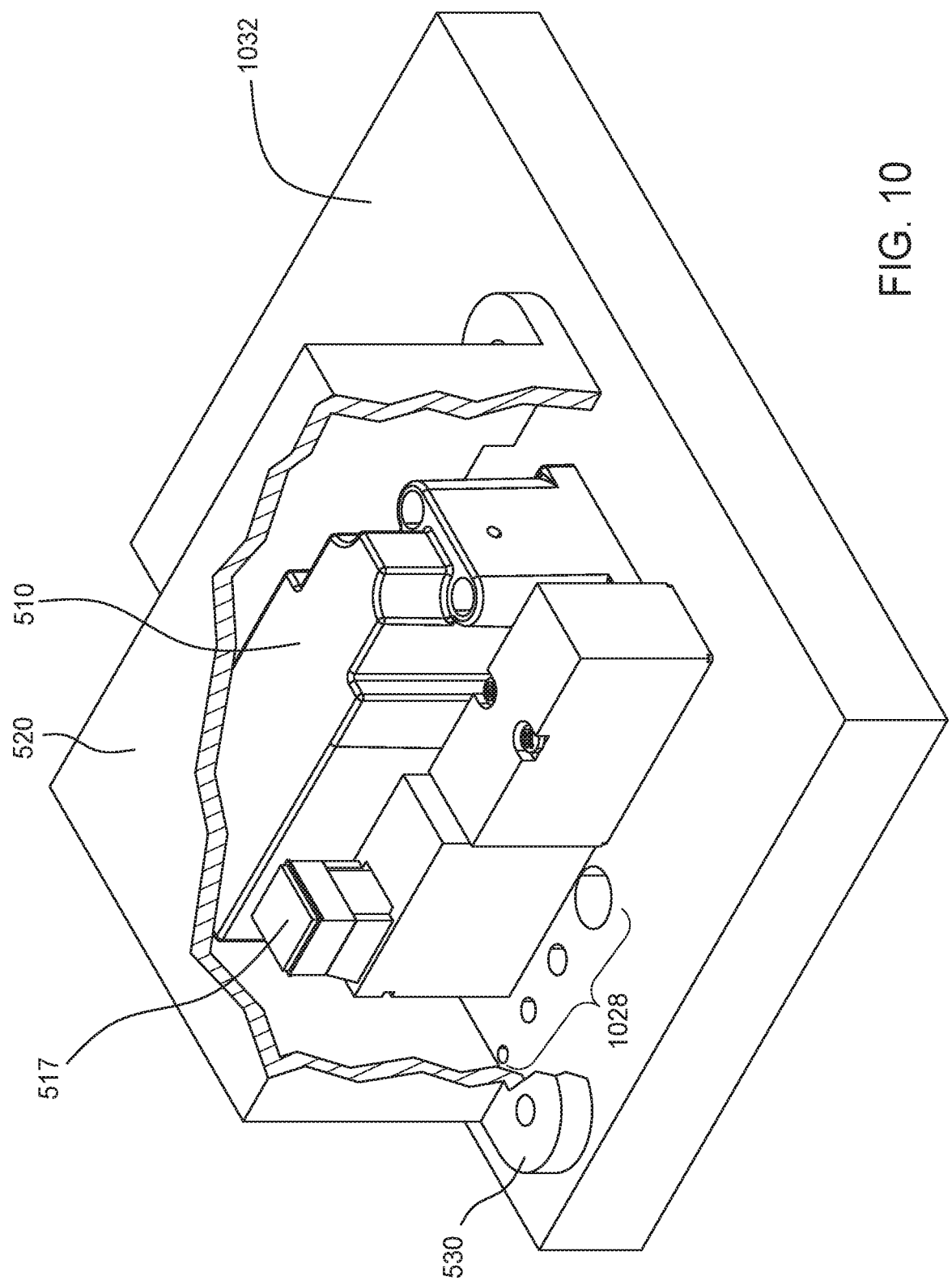
FIG. 10 illustrates multiple example inlet ports with different opening widths, in accordance with certain embodiments.

As described above, operating PPV 517 at a high valve cycle rate may cause the pneumatic valve to overheat and generate loud noise. Cover 520 is configured to circulate pressurized gas around the exterior of PPV 517 and isolation valve 510 for cooling purposes. In one example, the pressurized gas is provided through an inlet port 528 at one end of an exhaust pathway 526 that connects to an exhaust port 524 associated with PPV 517. In certain embodiments, inlet port 528 is created by drilling through manifold 532 and creating exhaust pathway 526 to connect inlet port 528 and exhaust port 524. Inlet port 528 may have different shapes (e.g., circular, linear, etc.) and sizes in different embodiments. In certain embodiments, instead of a single inlet port, multiple inlet ports may be used. FIGS. 8-10 show some example variations of the different shapes, sizes, numbers of inlet ports. An inlet port may also be referred to as an aperture.

Exhaust port 524 refers to an exhaust port of (e.g., exhaust port 422 of FIGS. 4A-4B) PPV 517 through which PPV 517 releases pressurized gas. Cover 520 is shaped such that pressurized gas, venting through inlet port 528 and into the space underneath cover 520, circulates around PPV 517 and isolation valve 510 and, thereby, cools PPV 517 and isolation valve 510. The space underneath cover 520 is formed by the inner surface of cover 520 (e.g., inner surface of all sides of cover 520) and the outer surface of manifold 532. The outer surface of manifold 532 refers to an area of the manifold that is covered by cover 520.

As shown, cover 520 also comprises an exhaust opening 522 to allow the pressurized gas to exit from the space underneath cover 520. In certain cases, pressurized gas exiting exhaust opening 522 creates undesired noise. As such, in some embodiments, cover 520 as well as exhaust opening 522 are shaped such as to reduce or suppress the generated noise. Additionally, one or more components (e.g., filtering material) may be placed outside of exhaust opening 522 to further reduce noise. For example, a component may be positioned outside of exhaust opening 522 to cover the opening. An example of a component that may be used outside of exhaust opening 522 may include open cell foam, reticulated foam, metal screen/mesh, perforated metal/plastic, sintered metal/plastic, (filter) paper, etc.

In one example, exhaust opening 522 refers to a rectangular opening at the bottom of one of the sides of cover 520, shown as side 521. Side 521 faces another side 519 of cover 520. Inlet port 528 is positioned between side 519 and PPV 517. In other examples, exhaust opening 522 may refer to other types of openings with other shapes in other areas of cover 520. In certain embodiments, the shape and size of exhaust opening 522 are designed to allow exhaust opening 522 to gradually slow the speed of the expanding gas in order to reduce the noise level associated with the pressurized gas. Also, cover 520 is configured to act as a muffler by allowing the pressurized gas exiting from inlet port 528 to expand, thereby attenuating the gas's pressure. In some embodiments, the cover 520 also suppresses noise generated by mechanical movement or actuation of the solenoid valves inside by enclosing such a noise source with noise absorbing materials. Note that although a single exhaust opening 522 is shown in FIG. 5, in certain embodiments, cover 520 may comprise multiple exhaust openings. In addition, the size, shape, and length of the exhaust opening may vary in different embodiments.

Cover 520 also comprises one or more fasteners for mounting cover 520 to manifold 532. An example of a fastener is shown in FIG. 5 as fastener 530, which may be screwed to manifold 532. A top view of fastener 530 is shown as fasteners 530a and 530b in FIG. 6.

Although in FIG. 5 exhaust port 524 refers to an exhaust port of PPV 517, in certain embodiments, exhaust port 524 represents a shared outlet for the exhaust ports of PPV 517 (e.g., exhaust port 422 of PPV 420 FIGS. 4A-4B) as well as a BPV (e.g., exhaust port 423 of BPV 430 FIGS. 4A-4B), which may be positioned under cover 520 with PPV 517. In other words, in such an example, exhaust port 524 vents pressurized gas exiting through the exhaust ports of PPV 517 and the BPV. In one example, pressurized gas exiting from the exhaust ports of PPV 517 and the BPV may be combined through one or more exhaust pathways incorporated into manifold 532. The one or more exhaust pathways may then intersect at exhaust port 524.

In certain other embodiments, exhaust port 524 represents a shared outlet for the exhaust ports of not only PPV 517 and BPV but also isolation valve 510. In other words, in such an example, exhaust port 524 vents pressurized gas exiting through the exhaust ports of PPV 517 and BPV (e.g., exhaust ports 422 and 423 of FIGS. 4A-4B) as well as isolation valve 510 (e.g., exhaust ports 421 FIGS. 4A-4B). Also, in such an example, pressurized gas exiting from the exhaust ports of isolation valve 510 and PPV 517 and BPV may be combined through one or more exhaust pathways that connect all the exhaust ports together.

In another example, exhaust port 524 represents a shared outlet for the exhaust port of isolation valve 510 and the exhaust port of only one of PPV 517 and BPV (e.g., PPV 420 of FIGS. 4A-4B). Also, although in FIG. 5 isolation valve 510 is located under cover 520, in certain embodiments, isolation valve 510 may be outside cover 520. In such embodiments, cover 520 may be smaller in size. Also, in certain embodiments, PPV 517 and BPV may both be positioned under cover 520 and, in certain other embodiments, only a single one of PPV 517 and BPV may be positioned under cover 520.

Further, FIG. 5 shows a single manifold plate, shown as manifold 532, through which exhaust pathway 526 and inlet port 528 are created (e.g., by drilling). However, in some embodiments, more than one manifold plate may be used. In such embodiments, an exhaust pathway and an inlet port similar to exhaust pathway 526 and inlet port 528 may be created in the two manifold plates. For example, in some embodiments, two manifold plates may be used on top of each other, where a seal may be used in between the two plates to ensure that the pressurized gas does not escape an exhaust pathway created in the two manifold plates. In some other embodiments, three manifold plates may be used with a seal between each two plates. In such embodiments, an exhaust pathway and an inlet similar to exhaust pathway 526 and inlet 528 may be created in the manifold plates.

Although the pneumatic system of FIG. 5 involves a redundant pneumatic circuitry (e.g., shown in FIGS. 4A-4B), in certain embodiments, a cover may be used for cooling and noise suppression in conjunction with a pneumatic system that does not involve a redundant pneumatic circuitry. An example of such a system was described in relation to FIGS. 2A and 2B. In such embodiments, a cover, similar to cover 520, is used to cool and suppress any noise generated by a pneumatic valve (e.g., pneumatic valve 217 of FIGS. 2A-B). More specifically, pressurized gas exiting from the pneumatic valve's exhaust port (e.g., similar to exhaust port 524) is vented into the space underneath the cover to cool the pneumatic valve. The pressurized gas then exits the cover's exhaust opening, which is configured to suppress the noise associated with the pressurized gas. In some embodiments, the cover 520 also suppresses noise generated by mechanical movement or actuation of the solenoid valve inside by enclosing such a noise source with noise absorbing materials. In cases where an isolation valve is coupled to the pneumatic valve of FIGS. 2A and 2B, the isolation valve may also be positioned underneath the cover. In such cases, PPV 517 and isolation valve 510 shown in FIG. 5, and later in FIGS. 7A-11, may represent pneumatic valve 217 of FIGS. 2A-2B and an isolation valve coupled to pneumatic valve 217, respectively. Note that the embodiments described herein are applicable regardless of the number of valves covered by the cover (e.g., cover 520). For example, in one example, only a single valve may be covered and in other examples, multiple valves (two, three, or more) may be covered. Also, the embodiments described herein are applicable regardless of the type or functionality of the pneumatic valve(s) and/or isolation valve positioned under the cover. In other words, although the pneumatic valve(s) and/or isolation valve described herein are used in conjunction with a pneumatically powered ophthalmic surgical machine, the embodiments of the present disclosure are applicable for cooling and noise suppression associated with any type of pneumatic valve and/or isolation valve used in conjunction with any machines or devices.

Figure 6:
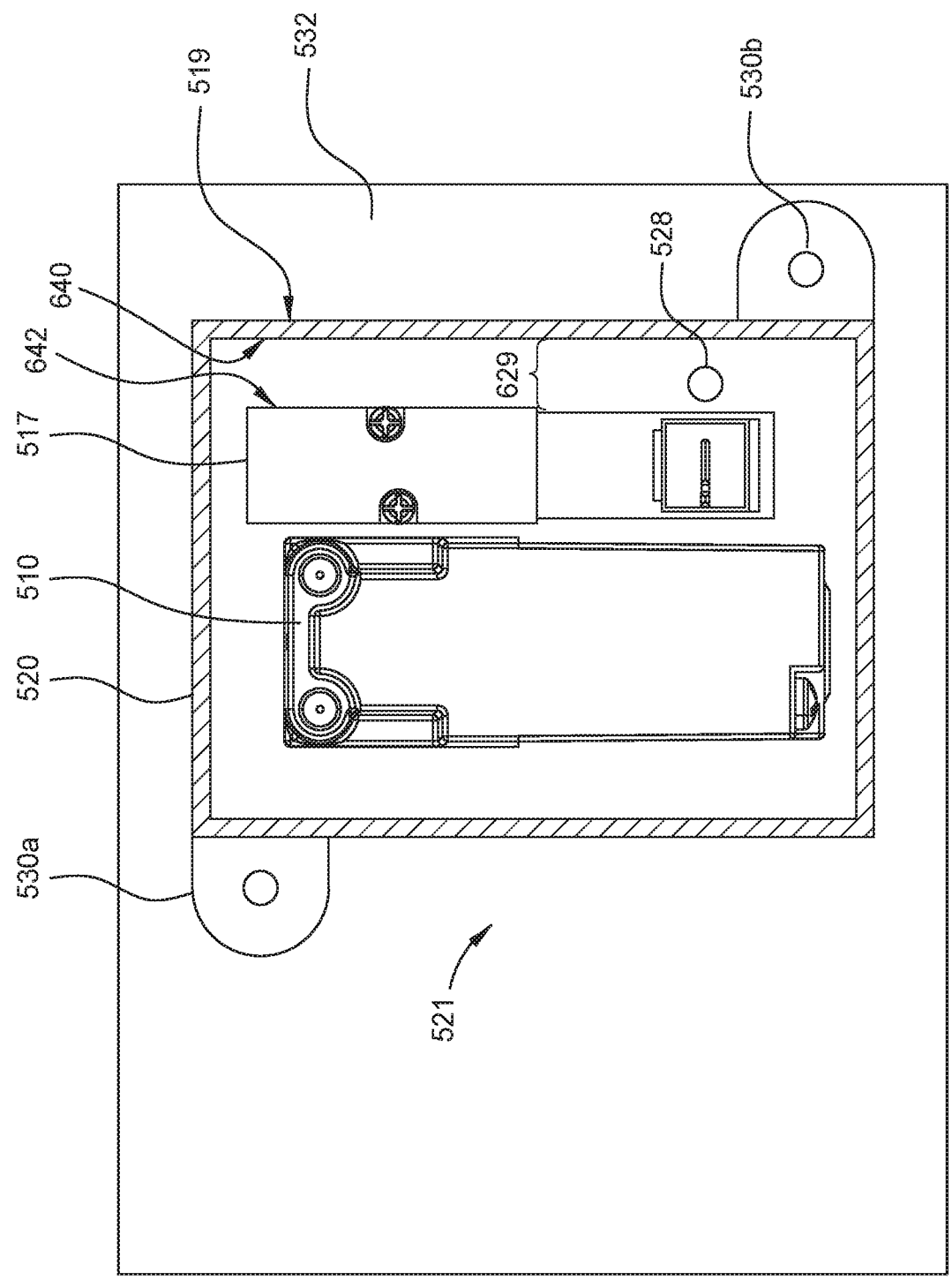
FIG. 6 illustrates a top cross-sectional view of an isolation valve, a single pneumatic valve, and cover, all mounted on top of the manifold of FIG. 5, in accordance with certain embodiments.

FIG. 6 illustrates a top cross-sectional view of an isolation valve 510, a single PPV 517, and cover 520, all mounted on top of manifold 532. As shown, cover 520 comprises two fasteners 530a and 530b for mounting cover 520 to manifold 532. Between PPV 517 and side 519 of cover 520 is an inlet port 528 from which pressurized gas is vented into the space underneath cover 520 for cooling PPV 517 and/or isolation valve 510. The pressurized gas then exits from an exhaust opening from the other side 521 of cover 520. As shown, the distance between inner surface 640 of side 519 of cover 520 and the side 642 of PPV 517 is configured such that the pressurized gas exiting from inlet port 528 is forced to flow near or onto the surface or exterior of PPV 517. The distance, in FIG. 6, is shown as distance 629. In one example, distance 629 is one-eighth of an inch. Generally, the distance is large enough to allow for the pressurized gas exiting inlet port 528 to expand such that pressure does not build up underneath the cover. The distance is also small enough to ensure that the pressurized gas does not expand away from PPV 517.

Figure 7A:
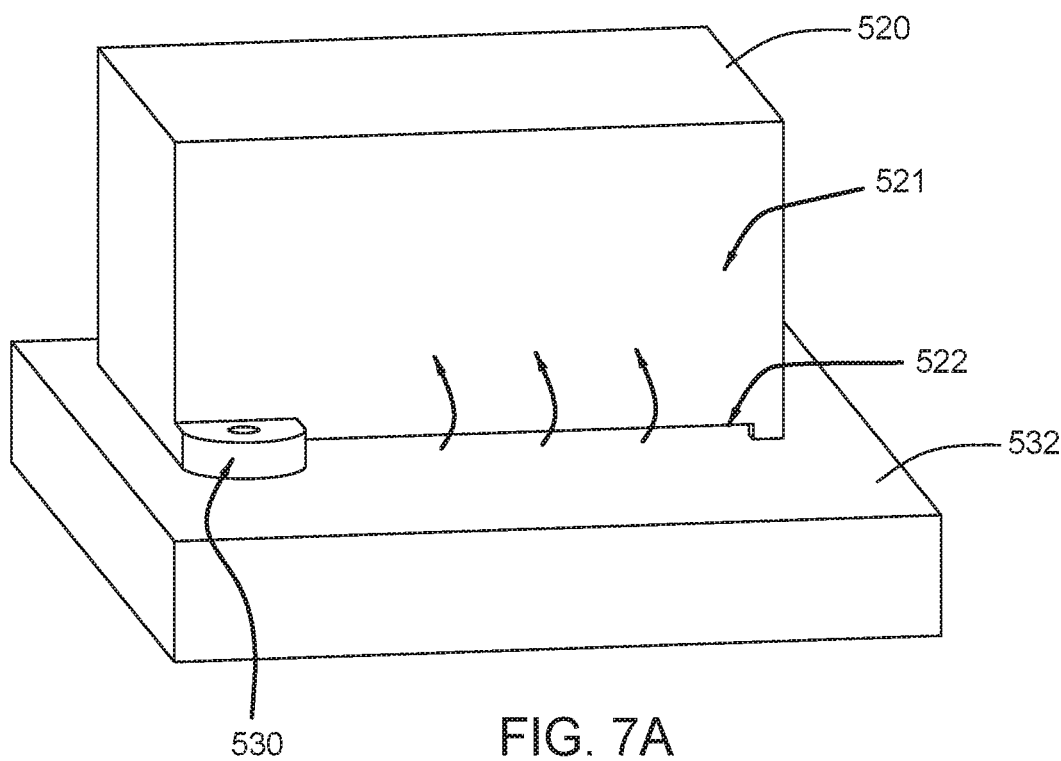
FIG. 7A illustrates a three-dimensional view of the cover of FIG. 5 mounted on top of a manifold, in accordance with certain embodiments.
Figure 7B:
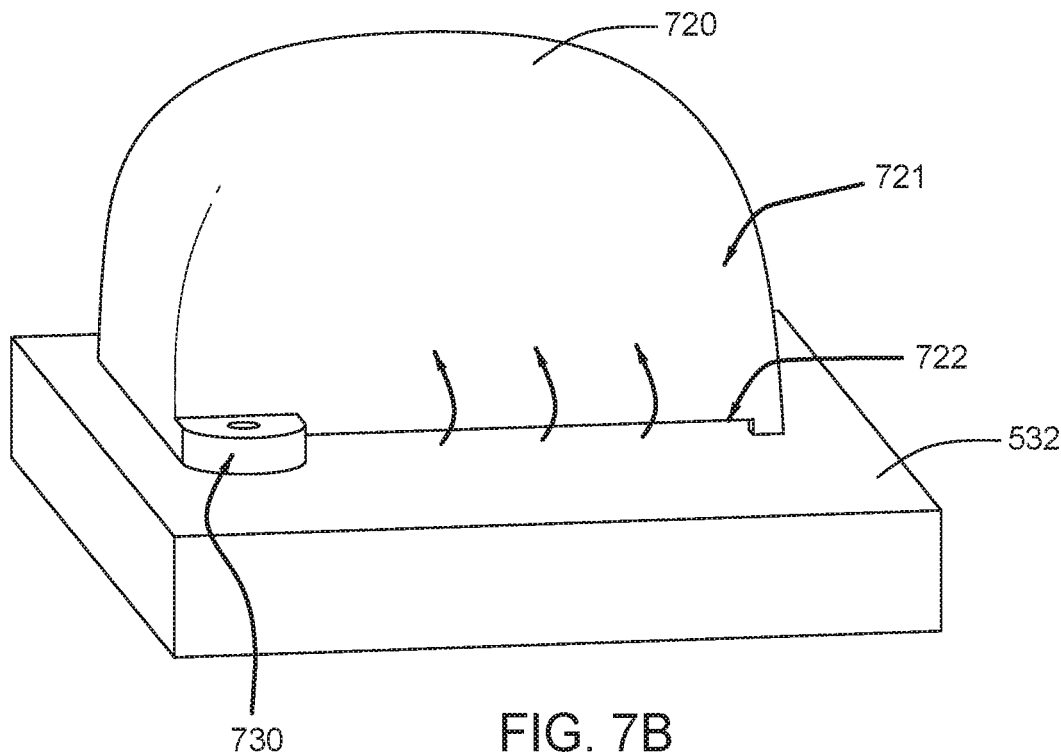
FIG. 7B illustrate a three-dimensional view of a dome shaped cover mounted on top of a manifold, in accordance with certain embodiments.

FIG. 7A illustrates a three-dimensional view of cover 520 that is mounted on top of manifold 532. As shown, cover 520 is a five-sided box, with an open bottom, that is mounted on manifold 532 using fastener 530. The open bottom of cover 520 is configured to receive PPV 517 and isolation valve 510. On its side 521, cover 522 provides an exhaust opening 522 through which pressurized gas exits the space underneath cover 520. Although shown as a box with a rectangular shape, cover 520 may have different shapes and sizes. As seen in FIG. 7B, a dome-shaped cover may be used in some embodiments. In some embodiments, the dome may be an oval-shaped dome.

FIGS. 8-10 illustrate different examples of one or more inlet ports through which pressurized gas is vented into the space underneath cover 520.

FIG. 8 illustrates an inlet port 828 that is slotted. A slotted inlet port 828 may be advantageous from a sound attenuation standpoint by focusing sound along a single plane or slotted inlet port 828 and/or from a cooling standpoint by supplying a solid curtain of air over the valve 517 and/or from a manufacturing standpoint (e.g., a slotted inlet port may be simpler to fabricate than a hole(s)). Although only a single slotted inlet port 828 is shown in FIG. 8, in certain embodiments, multiple slotted inlet ports may be used.

FIG. 9 illustrates inlet ports 928 that are arranged next to each other. In certain embodiments, all inlet ports 928 are fed from the same exhaust pathway (e.g., exhaust pathway 526) that connects with the exhaust port associated with PPV 517 and/or isolation valve 510. Note that the number, size, and shaped of inlet ports 928 may vary in different embodiments. Also, in certain embodiments, a combination of different sizes and shapes of inlet ports may be used. For example, in embodiments where multiple inlet ports are used, one inlet port may be slotted while others may be circular. Using inlet ports 928 may be advantageous from a sound attenuation standpoint (e.g., the size of holes or inlet ports 928 can be selected to reduce or break-up the sound coming out of the passage), and/or from a cooling standpoint (e.g., inlet ports 928 may provide a precise control of air flow to certain locations), and/or from a manufacturing standpoint (if less airflow is desired, then fabricating a small hole or series of holes may be easier).

FIG. 10 illustrates multiple inlet ports 1028 with different opening widths. In certain embodiments, all inlet ports 1028 are fed from the same exhaust pathway that connects with the exhaust port(s) associated with PPV 517 and/or isolation valve 510. Using inlet ports 1028 may be advantageous from a sound attenuation standpoint (e.g., using different hole sizes in different locations may be more effective for sound attenuation purposes than using a uniform hole size/pattern (e.g., inlet ports 928)), and/or from a cooling standpoint (e.g., changing the opening width allows more/less air to flow to a certain location).

In certain embodiments, an inlet port, such as the inlet ports illustrated in FIGS. 5-10, may comprise filtering material to suppress noise. As an example, filtering material may be placed within or on an inlet port. Examples of filtering material may include a screen, perforations, a mesh, an open cell foam, sintered material, etc.

Figure 11:
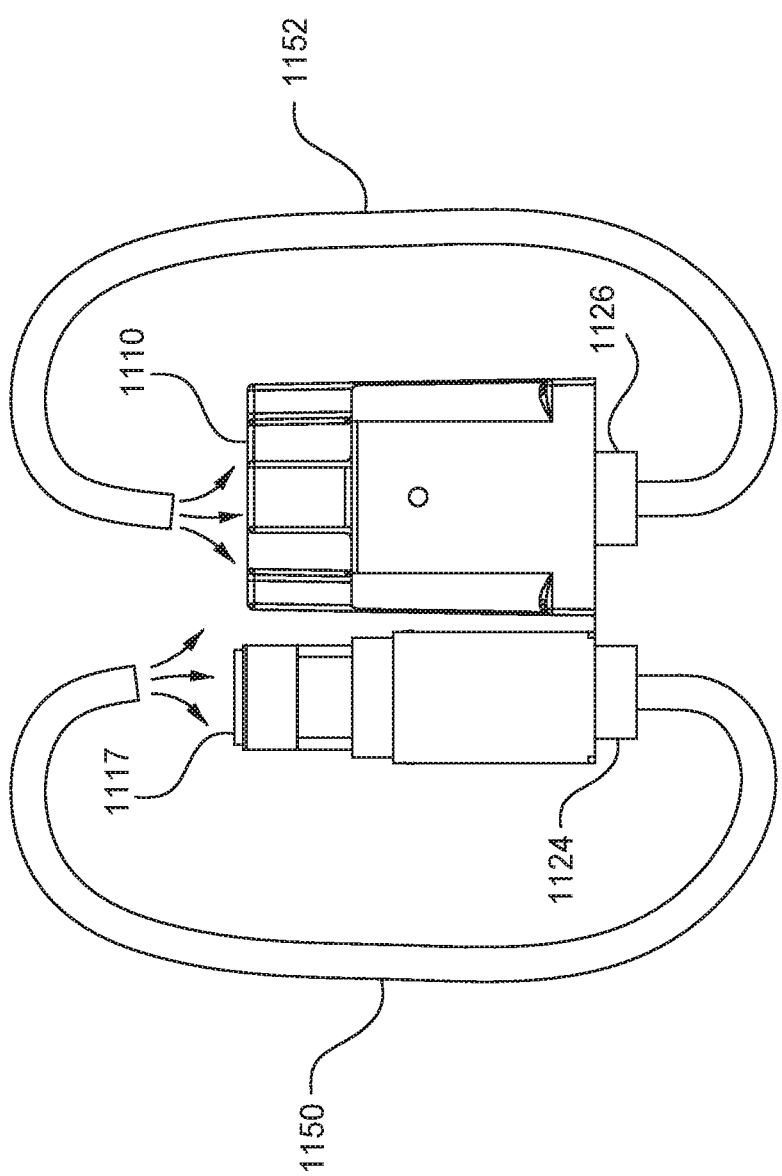
FIG. 11 illustrates example tubes coupled to exhaust ports of a pneumatic valve and an isolation valve for cooling purposes, in accordance with certain embodiments.

FIG. 11 illustrates an alternative embodiment for cooling PPV 1117 as well as isolation valve 1110, which are part of a redundant pneumatic circuitry whose other components are not shown for simplicity. Also, FIG. 11 does not illustrate a manifold on which PPV 1117 and isolation valve 1110 are mounted. In FIG. 11, exhaust port 1124 of PPV 1117 is coupled to a tube 1150 that blows pressurized gas exiting from exhaust port 1124 onto the exterior of PPV 1117. Tube 1150 may also be referred to as an exhaust pathway. More specifically, instead of creating an exhaust pathway through one or more manifolds to direct the pressurized gas exiting from exhaust port 1124 to an inlet port next to PPV 1117, in the embodiments of FIG. 11, tube 1150 is used to direct the pressurized gas exiting from exhaust port 1124 onto the exterior of PPV 1117. In certain embodiments, tube 1150 is not incorporated into the one or more manifolds while, in certain other embodiments, tube 1150 is incorporated into the one or more manifolds on top of which PPV 1117 is mounted. In one example tube 1150 is a plastic gas tube.

As shown in FIG. 11, exhaust port 1126 of isolation valve 1110 is coupled to a tube 1152 that blows pressurized gas exiting from exhaust port 1126 onto the exterior of isolation valve 1110. In certain embodiments, tube 1152 is not incorporated into the one or more manifolds while, in certain other embodiments, tube 1152 is incorporated into the one or more manifolds on top of which isolation valve 1110 is mounted. In one example, tube 1152 is a plastic gas tube.

Although in the embodiments of FIG. 11 a separate tube is coupled to each of the exhaust ports 1124 and 1126 of PPV 1117 and isolation valve 1110, in certain other embodiments a single tube may be coupled to both exhaust ports 1124 and 1126 through a connector element and blow pressurized gas exiting from exhaust ports 1124 and 1126 onto one or both of PPV 1117 and isolation valve 1110.

Although the pressurized gas exiting tubes 1150 and 1152 are able to cool PPV 1117 and isolation valve 1110, the gas flow creates some undesired noise. As such, in certain embodiments, a cover, similar to cover 520 of FIG. 5, may be used to not only ensure circulation of the pressurized gas around the PPV 1117 and isolation valve 1110, resulting in more effectively cooling the valves, but also suppress the noise associated with the exhaust gas. In certain embodiments, the cover also suppresses noise generated by mechanical movement or actuation of the solenoid valves inside by enclosing such a noise source with noise absorbing materials. In certain embodiments, the cover is mounted on top of PPV 1117 and isolation valve 1110 with two openings to allow tubes 1150 and 1152 to exit the cover and two other openings to allow the tips of the tubes 1150 and 1152 to enter the cover again. The cover also comprises an exhaust opening, similar to exhaust opening 522, to allow the pressurized gas to exit the space underneath the cover. In embodiments where the tubes are incorporated into the manifold, the cover may only comprise two openings to allow the tips of tubes 1150 and 1152 to enter the cover. The tubes 1150 and 1152 may accordingly act as inlets for gas to the space defined by the cover. Note that an inlet may refer to an inlet port (e.g., inlet ports 528, 828, 928. 1028) or a tube (e.g., tube 1150 and 1152).

Note that although the isolation valve (e.g., 510 or 1110) shown in FIGS. 5-11 is an isolation valve that is used in conjunction with a redundant pneumatic circuit, as shown in FIGS. 4A-4B, in certain embodiments, an isolation valve that is positioned under the cover 520 described herein may not be an isolation valve that is used in a redundant pneumatic circuitry. For example, in certain cases, an isolation valve may be used in conjunction with a pneumatic system that does not involve a redundant pneumatic circuitry (e.g., FIGS. 2A-2B). Also, in certain embodiments, an isolation valve that is positioned under the cover 520 described herein may not be a four-way valve, such as shown in FIGS. 4A-4B. For example, the isolation valve may be a three-way valve or any other type of isolation valve. In other words, the embodiments described herein with respect to FIGS. 5-11 are applicable regardless of the type and use of an isolation valve that is positioned under cover 520.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A cover mounted on top of a manifold, the cover comprising:
   an exhaust opening; and
   an inner surface forming a space between the inner surface of the cover and an outer surface of the manifold, wherein:
   the space is configured to receive pressurized gas at an inlet positioned on a first side of a valve;
   the valve is coupled to the outer surface of the manifold and positioned within the space; and
   the exhaust opening is positioned on a second side of the valve opposite the first side of the valve such that the pressurized gas circulates from the inlet around the valve and exits through the exhaust opening;
   wherein a second valve is coupled to the outer surface of the manifold and positioned within the space;
   wherein:
   the inlet comprises an inlet port,
   the inlet port is connected to an exhaust port of the valve through a passage in the manifold, and
   the pressurized gas is released from the valve through the exhaust port.

2. The cover of claim 1, wherein:
   the inlet port is positioned between a first side of the cover and the first side of the valve; and
   a second side of the cover comprises the exhaust opening.

3. The cover of claim 1, wherein the cover is rectangular in shape with an open bottom, wherein the open bottom of the cover is configured to receive the valve.

4. The cover of claim 1, wherein the cover comprises a dome with an open bottom, wherein the open bottom of the cover is configured to receive the valve.

5. The cover of claim 4, wherein the cover comprises an oval-shaped dome.

6. The cover of claim 1, wherein:
   the pressurized gas is released from the valve and the second valve through the exhaust port,
   the exhaust port is shared between the valve and the second valve.

7. A cover mounted on top of a manifold, the cover comprising:
   an exhaust opening; and
   an inner surface forming a space between the inner surface of the cover and an outer surface of the manifold, wherein:
   the space is configured to receive the pressurized gas at an inlet positioned on a first side of a valve;

the valve is coupled to the outer surface of the manifold and positioned within the space; and the exhaust opening is positioned on a second side of the valve opposite the first side of the valve such that pressurized gas circulates from the inlet around the valve and exits through the exhaust opening;

wherein a second valve is coupled to the outer surface of the manifold and positioned within the space;

wherein:

the inlet comprises a tube, the tube is connected to an exhaust port of the valve, and the pressurized gas is released from the valve through the exhaust port.

8. A pneumatic system, comprising:

a tool with a first chamber and a second chamber on respective sides of a pneumatically driven diaphragm for reciprocating a component of the tool;

a pressurized gas source;

a valve coupled to the pressurized gas source, the valve having a solenoid which, when supplied with a current, moves a solenoid plunger to alternatively deliver and vent pressurized gas through a first outlet line and a second outlet line which respectively deliver and vent pressurized gas to and from the first chamber and to and from the second chamber of the tool;

a power supply coupled to the solenoid of the valve for supplying a voltage to drive a current in the solenoid;

a manifold on top of which the valve is mounted;

a cover mounted on top of the manifold, wherein the cover comprises:

an exhaust opening; and an inner surface forming a space between the inner surface of the cover and an outer surface of the manifold, wherein:

the space is configured to receive the pressurized gas at an inlet positioned on a first side of a valve;

the valve is coupled to the outer surface of the manifold and positioned within the space, and the exhaust opening is positioned on a second side of the valve opposite the first side of the valve such that pressurized gas circulates from the inlet around the valve and exits through the exhaust opening.

9. The pneumatic system of claim 8, wherein:

the inlet comprises an inlet port, the inlet port is connected to an exhaust port of the valve through a passage in the manifold, and the pressurized gas is released from the valve through the exhaust port.

10. The pneumatic system of claim 9, wherein:

the inlet port is positioned between a first side of the cover and the first side of the valve, and a second side of the cover comprises the exhaust opening.

11. The pneumatic system of claim 8, wherein the cover is rectangular in shape with an open bottom, wherein the open bottom of the cover is configured to receive the valve.

12. The pneumatic system of claim 8, wherein the cover comprises a dome with an open bottom, wherein the open bottom of the cover is configured to receive the valve.

13. The pneumatic system of claim 12, wherein the cover comprises an oval-shaped dome.

14. The pneumatic system of claim 8, wherein:

the inlet comprises a tube, the tube is connected to an exhaust port of the valve, and the pressurized gas is released from the valve through the exhaust port.

15. The pneumatic system of claim 8, wherein a second valve is coupled to the outer surface of the manifold and positioned within the space.

16. The pneumatic system of claim 15, wherein:

the inlet comprises an inlet port, the inlet port is connected to an exhaust port of the valve through a passage in the manifold, the pressurized gas is released from the valve through the exhaust port, and the exhaust port is shared between the valve and the second valve.

17. The pneumatic system of claim 8, further comprising an isolation valve and a control system, wherein:

the control system is configured to actuate the isolation valve to selectively allow pneumatic pressure to flow to the valve and suppress pneumatic pressure to a backup valve and suppress pneumatic pressure to flow to the valve and allow pneumatic pressure to the backup valve, the isolation valve is coupled to the outer surface of the manifold and positioned within the space.

18. The pneumatic system of claim 17, wherein:

the inlet comprises an inlet port, the inlet port is connected to an exhaust port of the valve through a passage in the manifold, the pressurized gas is released from the valve through the exhaust port, the exhaust port is shared between the valve and the second valve.

* * * * *